United States Patent
Davis et al.

(10) Patent No.: US 7,780,853 B2
(45) Date of Patent: *Aug. 24, 2010

(54) METHOD FOR CONDUCTING MAINTENANCE ON A CHROMATOGRAPHY COLUMN

(75) Inventors: John Davis, Amersham (GB); Stefan K. Eriksson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 481 days.

This patent is subject to a terminal disclaimer.

(21) Appl. No.: 11/834,864

(22) Filed: Aug. 7, 2007

(65) Prior Publication Data

US 2009/0039008 A1   Feb. 12, 2009

Related U.S. Application Data

(63) Continuation-in-part of application No. 11/763,477, filed on Jun. 15, 2007, now Pat. No. 7,708,891.

(51) Int. Cl.
   *B01D 15/08*   (2006.01)
(52) U.S. Cl. ..................... 210/656; 210/198.2

(58) Field of Classification Search ............. 210/635, 210/656, 659, 198.2; 95/82; 96/101
See application file for complete search history.

(56) References Cited

U.S. PATENT DOCUMENTS

| 5,167,809 | A | * | 12/1992 | Mann et al. | ............. | 210/198.2 |
| 6,001,260 | A | * | 12/1999 | Hatch et al. | ............. | 210/656 |
| 6,736,974 | B1 | | 5/2004 | Mann | | |
| 7,041,216 | B2 | * | 5/2006 | Dunkley et al. | ............. | 210/198.2 |
| 7,604,747 | B2 | * | 10/2009 | Spencer et al. | ............. | 210/656 |
| 2009/0078634 | A1 | * | 3/2009 | Dunkley et al. | ............. | 210/198.2 |

FOREIGN PATENT DOCUMENTS

WO   WO2005/056156   6/2005

* cited by examiner

*Primary Examiner*—Ernest G Therkorn
(74) *Attorney, Agent, or Firm*—Yonggang Ji

(57) ABSTRACT

The present invention relates to methods for conducting maintenance on chromatography columns used in industrial-scale chromatography. In particular, the invention is concerned with safer methods for performing maintenance on such columns, such as cleaning and replacing bed supports, distributors, nozzles, O-rings and other column components, by the use of a handling device to support, lift, carry and manipulate such column components.

11 Claims, 20 Drawing Sheets

METHOD FOR CONDUCTING MAINTENANCE ON A CHROMATOGRAPHY COLUMN

CROSS-REFERENCE TO RELATED APPLICATIONS

This application is a contiuation-in-part of allowed U.S. patent application Ser. No. 11/763,477 filed Jun. 15, 2007 now U.S. Pat. No. 7,708,891; the entire disclosure of which is incorporated herein by reference in its entirety.

FIELD OF THE INVENTION

The present invention relates to methods for conducting maintenance on chromatography columns used in industrial-scale chromatography. In particular, the invention is concerned with safer methods for performing maintenance on such columns, such as cleaning and replacing bed supports, distributors, O-rings and other column components, by the use of a handling device to support, lift, carry and manipulate such column components.

BACKGROUND OF THE INVENTION

Chromatography columns may be used in industrial processes to purify process liquids and separate substances of interest from process liquids; typical examples include large-scale preparative purification of fine chemicals and pharmaceuticals, together with biological products.

Industrial-scale chromatography columns typically comprise a hollow, axially vertical tubular housing including a liquid inlet at the upper end and through which the buffer and substances to be separated are dispensed to the media bed located within the cavity of the tube, and a liquid collecting system at the lower end for collecting substances and buffer. The particulate chromatographic media or bed through which the buffer fluid and/or substances to be separated and purified percolates is located between the liquid inlet and collecting system.

An adapter assembly is typically affixed to the upper end of the tubular housing and a base assembly to the lower end where it is bolted to the bottom flanges. Each of these assemblies typically comprises a strong backing plate and a distributor plate which further supports a bed support; a bed support is a layer of mesh, screen, filter, sinter or other fluid-permeable media-retaining material which permits process liquid flow into and out of the chromatography bed space or cavity while retaining the bed of particulate medium. To provide adjustability and control of the bed height and bed compression, the adapter assembly is typically made in the form of a piston or sliding adapter in the column tube interior. After the column is charged with bed media, typically through a nozzle, the adapter may be forced toward the bottom of the tube to compress or pressurize the media bed. Generally the base assembly is a fixed structure which is bolted against the bottom flange of the column tube but, in some instances, may also be in the form of a movably slidable piston or adapter.

The backing plate of the base assembly generally acts as a support for the column, being itself supported on legs or some other stand arrangement which allows clearance for outlet pipework projecting beneath the base assembly.

When such a column requires maintenance to, or cleaning of, internal components, such as the valves, seals, meshes/screens, distribution systems etc., heavy lifting gear such as a crane or hoist is necessary to lift the upper end/adapter assembly away from the column tube and the column tube away from the lower end/base assembly as these assemblies can weigh in excess of three tons. Lifting of these assemblies then provides access to the internal column components, but often it is necessary to remove some of these components prior to maintenance. As these components can be very heavy (bed supports, for example, may weigh in excess of 100 kg), their manual removal and re-introduction poses a potential safety risk to operators who must physically support and manipulate them.

The use of heavy overhead lifting equipment to disassemble the column in order to carry out internal maintenance is, in itself, highly undesirable. Operator safety is obviously a concern when heavy equipment is lifted overhead and technicians exposed below. Furthermore, alignment structures are required to keep the column and its base/adapter assemblies axially aligned as they are separated from each other, to avoid damage to the precision components. Moreover, the requirement to use heavy lifting equipment imposes constraints on housing such columns, sufficient overhead space and support being required to accommodate hoists or cranes. Further, the presence of such hoists or cranes in GMP facilities used for biopharmaceutical manufacturing (such facilities also being known as "clean rooms") is highly undesirable due to the shedding of particulate matter such as dirt during their operation and maintenance.

U.S. Pat. No. 6,736,974 addresses some of the above problems by providing a column which is capable of lifting the adapter assembly above the column tube and/or raising the column tube above the base assembly by means of an hydraulic system which is integral to the column.

However, the system described in U.S. Pat. No. 6,736,974 has significant disadvantages associated with it by virtue of its design. As can be seen from FIGS. 4 and 5 of U.S. Pat. No. 6,736,974 and described in column 4, lines 63-66 of that document, in order to remove the distributor plate (31) and/or bed support/mesh (28/60) from the interior of the column, the operator must work within the centre of the drum (18) to access and remove the fixing nut (30) which secures these component parts. As industrial columns typically have diameters ranging from about 200 mm to 2000 millimetres, this means that the operator must work below a suspended or supported load to unscrew the nut. This clearly poses a significant safety risk to the operator, particularly where the operator's arm or head is exposed below the suspended or supported load.

Furthermore, once the column tube/cylinder or adapter assembly has been raised from the base assembly or tube, respectively, removal of the heavy bed support or distributor from the column can only be accomplished by tilting the bed support or distributor at an angle to negotiate the hydraulic drive pistons or safety rods. This can clearly be seen from, for example, FIGS. 3, 4 and 5 in which the distance between any two safety rods (69) or between any two hydraulic pistons (36) is less than the diameter of the bed support/mesh (28/60) or distributor plate (31). The same problem would exist for the base or adapter bed support (not shown). Removal of these internal components, which could weigh in excess of 100 kg, requires considerable manhandling by the operator and necessitates their being exposed below the suspended column or adapter assembly. Once again, this represents a significant safety risk for the operator.

The task of physically removing the heavy bed support or distributor, as described in U.S. Pat. No. 6,736,974, must be carried out by an operator, there being no disclosure of the use of any lifting aid to assist in this task. The configuration of the hydraulic pistons and the safety rods, and the need to tilt the bed support and/or distributor in order to avoid the supporting structures in withdrawing these components from the column, makes their manual withdrawal and re-introduction a difficult and potentially dangerous task.

WO 2005/056156 (Euroflow (UK) Limited) also discloses a column which can be accessed for maintenance without the need for a crane or hoist. The column is designed such that the tube and the base assembly can be separated by means of hydraulic drive cylinders to provide an access space between them to conduct maintenance or service on the base assembly. The piston of the adapter assembly can be advanced through the column tube to expose it at the open end of the column tube, i.e. in the space between the tube and the base assembly, for maintenance.

However, as is evident from this document (for example, FIGS. 19 and 20 and related description on page 23) access to release the fastening screws retaining the bed support/mesh in place is provided by the space between the tube and the base assembly. Removal of the bed support/mesh necessitates the operator being exposed to a suspended load while retaining screws are removed. Furthermore, the distance between any two drive cylinders for maintenance access is less than the diameter of the bed support (see, for example, FIG. 7), which requires the operator to manhandle and tilt the mesh or bed support when removing or replacing it. Once again, there is no mention of the use of a handling device in the removal or re-introduction of column components. Maintenance of the column thus imposes a potential safety risk for the operator in physically supporting and manipulating the heavy column components.

U.S. patent application Ser. No. 11/763,477, entitled "Chromatography Column and Method of Maintenance", filed by the same applicants and hereby incorporated by reference in its entirety, describes a chromatography column which addresses some of the above problems.

Accordingly, a need exists to improve the maintenance methods available for chromatography columns by providing devices which facilitate the handling, manipulation and transportation of heavy column components without the need to work under suspended loads and thereby reduce the risk of operator error and injury.

SUMMARY OF THE INVENTION

The present invention recognizes and addresses these needs and others. In a first aspect of the present invention, there is provided a method for conducting maintenance on a chromatography column comprising the steps of:
a) providing a chromatography column comprising;
   a dispersion system comprising a nozzle including a mobile phase pathway connected to a liquid inlet;
   a tube with an adaptor assembly, said adapter assembly moveable within a cavity of said tube in an operational mode;
   the adapter assembly comprising, a distributor and a bed support fastened to each other by releasable fixing means,
   a collection system opposing the dispersion system; and one or more seals;
b) disconnecting the adapter assembly from the tube;
c) lifting the adapter assembly above the tube to provide a gap for access therebetween;
d) unfastening the bed support from the distributor by releasing the fixing means;
e) removing the bed support from the column with a handling device;

f) conducting maintenance on the column and/or the bed support and/or said one or more seals;
g) returning the bed support to the column with said handling device and fastening the bed support to the distributor; and
h) lowering the adapter assembly to an operational position within the tube and reconnecting the adapter assembly to the tube.

In one aspect, the method further comprises the step of removing the distributor from the column with the handling device and conducting maintenance on the column and/or said distributor.

In one aspect, the method further comprises the steps of removing said nozzle from the column with the handling device prior to step d) and returning the nozzle to the column with the handling device following step g).

Preferably, the handling device is in the form of a cart having a pillar and comprising one or more arms projecting from said pillar for supporting the bed support or the distributor or the nozzle thereon. Preferably, the arms are extendable from the pillar. More preferably, the arms are vertically movable on the pillar.

In one aspect, lifting the adapter assembly in step c) and/or lowering the adapter assembly in step h) is carried out by means of an overhead hoist or crane.

In another aspect, lifting the adapter assembly in step c) and/or lowering the adapter assembly in step h) is carried out by means of a drive system comprising one or more cylinders which are mounted to or are integral with the column.

Optionally, the method additionally comprises the step of removing said one or more cylinders from the column with the handling device.

Preferably, the step of removing the bed support from the column and/or the step of returning the bed support to the column with the handling device is carried out without substantially tilting the bed support. This reduces operator exposure beneath the suspended load and facilitates mechanical handling of the bed support. The term 'without substantially tilting' as used herein means 'tilting at an angle of no more than 5° to the horizontal'.

Optionally, the step of removing the bed support from the column and/or the step of returning the bed support to the column with the handling device is carried out by tilting the bed support at an angle of more than 5° to the horizontal. This may be necessary where the distance between any two drive cylinders is less than the diameter of the bed support.

In a second aspect of the present invention, there is provided a method for conducting maintenance on a chromatography column comprising the steps of:
a) providing a chromatography column comprising;
   a dispersion system comprising a nozzle including a mobile phase pathway connected to a liquid inlet;
   a tube with an adapter assembly and a base assembly, said adapter assembly moveable within a cavity of said tube in an operational mode;
   the base assembly comprising a distributor and a bed support fastened to each other by releasable fixing means;
   a collection system opposing the dispersion system; and one or more seals;
b) releasing the tube from the base assembly;
c) lifting the tube and the adapter assembly above the base assembly to provide a gap for access therebetween;
d) unfastening the bed support from the distributor by releasing the fixing means;
e) removing the bed support from the column with a handling device;

f) conducting maintenance on the column and/or the bed support and/or said one or more seals;

g) returning the bed support to the column with said handling device and fastening the bed support to the distributor; and h) lowering the tube and the adapter assembly and reconnecting the tube to the base assembly.

In one aspect, the method further comprises the steps of removing the distributor from the column with the handling device and conducting maintenance on the column and/or said distributor.

Preferably, the handling device is in the form of a cart having a pillar and comprising one or more arms projecting from said pillar for suspending the bed assembly or distributor thereon. Preferably, the arms are extendable from the pillar. More preferably, the arms are vertically movable on the pillar.

In one aspect, lifting the tube and the adapter assembly in step c) and/or lowering the tube and the adapter assembly in step h) is carried out by means of an overhead hoist or crane.

In another aspect, lifting the tube and the adapter assembly in step c) and/or lowering the tube and the adapter assembly in step h) is carried out by means of a drive system comprising one or more cylinders which are mounted to or are integral with the column.

Optionally, the method additionally comprises the step of removing said one or more cylinders from the column with the handling device.

Preferably, the step of removing the bed support from the column and/or the step of returning the bed support to the column with the handling device is carried out without substantially tilting the bed support. This reduces operator exposure beneath the suspended load and facilitates mechanical handling of the bed support. The term 'without substantially tilting' as used herein means 'tilting at an angle of no more than 5° to the horizontal'.

Optionally, the step of removing the bed support from the column and/or the step of returning the bed support to the column with the handling device is carried out by tilting the bed support at an angle of more than 5° to the horizontal. This may be necessary where the column has drive cylinders and the distance between any two drive cylinders is less than the diameter of the bed support.

In a third aspect of the present invention, there is provided a handling device for use in a method of conducting maintenance on a chromatography column as hereinbefore described, said device comprising a frame with wheels and a pillar, one or more arms projecting from said pillar for supporting or suspending a chromatography column component therefrom, said one or more arms being movable vertically along the axis of the pillar by mechanical means, wherein the one or more arms has an attachment means for securing said column component thereto. Optionally, the device may additionally comprise a handle to facilitate steering.

In one aspect, the chromatography column component is selected from the group consisting of bed support, distributor, nozzle and drive cylinder.

In another aspect, the attachment means is a raised element on the surface of the one or more arms for receipt of a fixing means in said column component. Preferably, the raised element is located centrally on one or more arms or at the intersection of the one or more arms. More preferably, the raised element is conically shaped to facilitate attachment of the column component to the arm.

In another aspect, the attachment means comprises a fixture for receipt of fixing means in the column component.

In a further aspect, the one or more arms additionally comprise a pad for resting the column component thereon. This prevents damage to the column component. Preferably, the one or more arms are extendable.

In a further aspect, the one or more arms are removable and replaceable with different arms to allow attachment of different column components.

In one aspect, the mechanical means for moving the one or more arms vertically along the axis of the pillar comprises a pulley or jack. Preferably, the mechanical means for moving the one or more arms vertically along the axis of the pillar is powered by electrical, pneumatic or hydraulic means.

In another aspect, the wheels are independently rotatable to improve the maneuverability of the handling device. Preferably, the wheels are independently lockable. Preferably, the wheels are independently levelable; for example, by means of jacking devices attached to each wheel. Levelable wheels provide easier and smoother operation of the handling device on surfaces which are uneven such as clean rooms with sloping floors. More preferably, the wheels are powered by electrical means.

In a particularly preferred aspect, the one or more arms can rotate or pivot about the axis of the pillar to facilitate removal of the bed support or distributor where the column has drive cylinders and the distance between any two cylinders is less than the diameter of the bed support or distributor.

BRIEF DESCRIPTION OF THE DRAWINGS

The features and advantages of the invention will become apparent from the following description taken in connection with the accompanying drawings in which:

FIG. 4b is a side sectional view of the column of FIG. 4a; and FIG. 4c is a top plan view of the column of FIG. 4a.

DETAILED DESCRIPTION OF THE PREFERRED EMBODIMENTS

Figure 1:
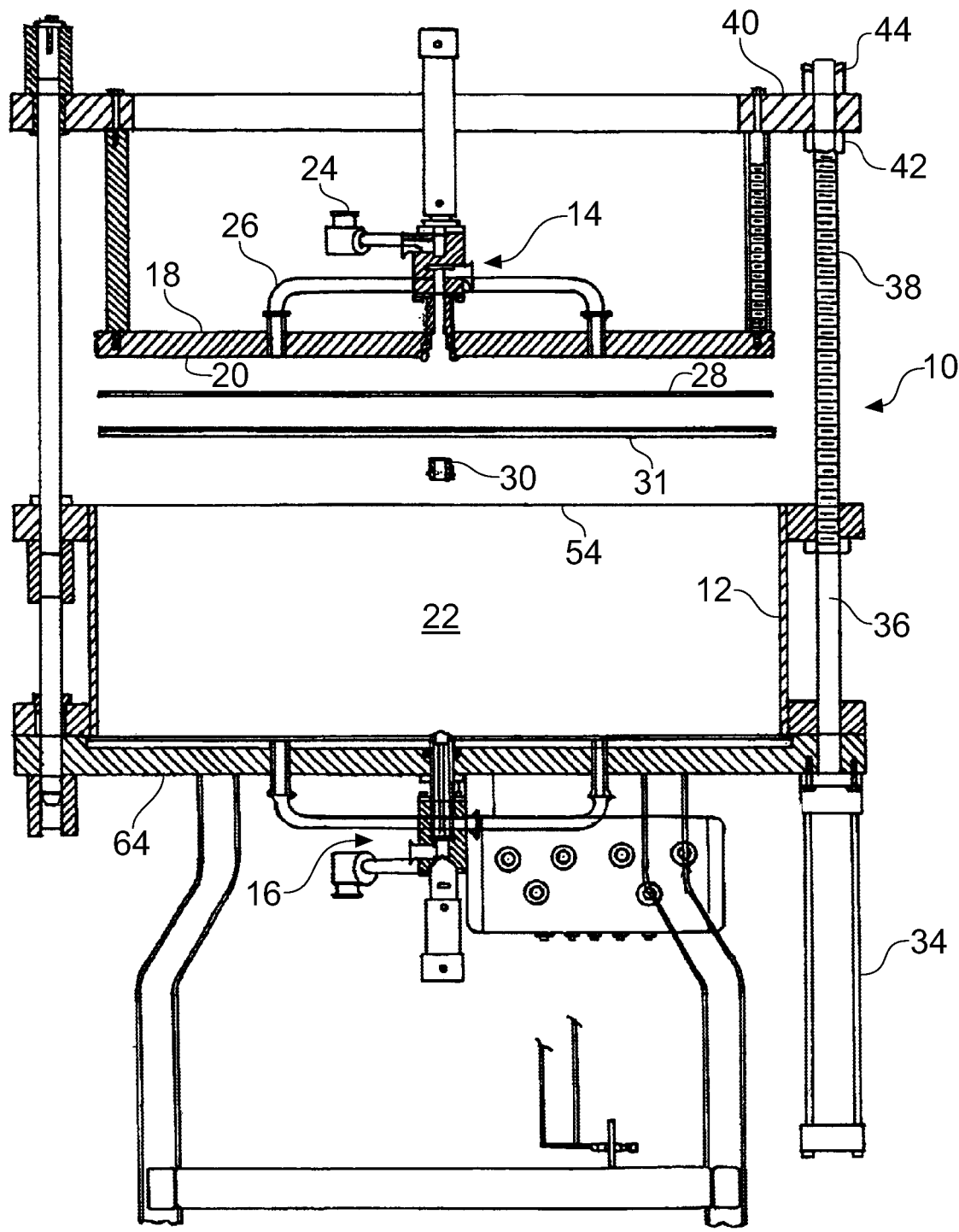
FIG. 1 shows an embodiment of a column known in the art in a first maintenance position in cross sectional view.

The present invention is concerned with a method and apparatus for conducting maintenance on a chromatography column. The invention is described by reference to chromatography columns which utilise drive systems to lift and/or lower the adapter assembly, and lift and/or lower the tube and adapter assembly. It will be understood that the invention could equally be described by reference to chromatography columns wherein these components are raised and/or lowered by an overhead hoist or crane. FIG. 1 shows a column 10 known in the art and described in U.S. Pat. No. 6,736,974 which permits maintenance within a chromatography column without the need for a hoist or crane. The column 10 comprises an elongated hollow cylindrical housing 12, or tube, having a dispersion system 14 at the top and a collection system 16 at the bottom. The dispersion system 14 includes a cylindrical drum 18 having an upper cylindrical plunger head or adapter 20 formed at the lower or interior end (i.e. interior to the column). The adapter 20 is normally disposed within the upper portion of tube 12 such as is illustrated in the first operational position of FIG. 1. The adapter 20 may be moved by a drive system 34 such as the hydraulic arrangement shown in FIG. 1. The movement of the adapter 20 allows for the compression of chromatography media in order to produce a packed media bed of the optimum height within the column; a cavity 22 is formed between the dispersion and collection systems 14, 16 and/or between the adapter 20 and the base 64.

The dispersion system 14 may include a mobile phase pathway connected to a liquid inlet 24 together with an inlet manifold 26 to distribute incoming liquid throughout a top portion of a media bed contained within the cavity 22. A bed support or inlet screen 28 is attached to the adapter 20 by connectors and/or by an inner clamp nut 30 which is accessible from the cavity 22. The bed support 28 may be removed manually for maintenance purposes by release of the clamp nut 30; the distributor plate 31 may also be manually removable (see U.S. Pat. No. 6,190,560 for a description of a distributor plate design).

A drive system is used to move the adapter 20 in an operational mode. The drive system is comprised of at least one and preferably three or more, drive cylinders 34. The drive cylinders 34 move drive pistons 36 which are coupled to the drum 18. A portion of the drive pistons 36 may by threaded 38 to allow for the drive piston 36 to connect or couple to connection arms 40 at specific locations relative to the drive piston 36 such as with nuts 42, 44.

FIG. 1 shows a first maintenance position of the adapter 20 wherein the adapter 20 is raised a predetermined distance from a top 54 of the cavity 22 within the cylinder by means of the drive system 34 and piston 36. The operator is thereby provided access with a hand to the centre of the drum 18 to release or affix nut 30 which retains the distributor plate 31 and bed support 28 to the adapter 20. The distributor plate 31 and or/bed support 28 may then be removed manually, without the use of a handling device, for maintenance. Once maintenance has been carried out, these components are then replaced by manual means, affixed to the adapter 20 and the adapter 20 lowered to return to an operational mode, nuts 42, 44 being reset to a proper operational configuration, if necessary.

Figure 2:
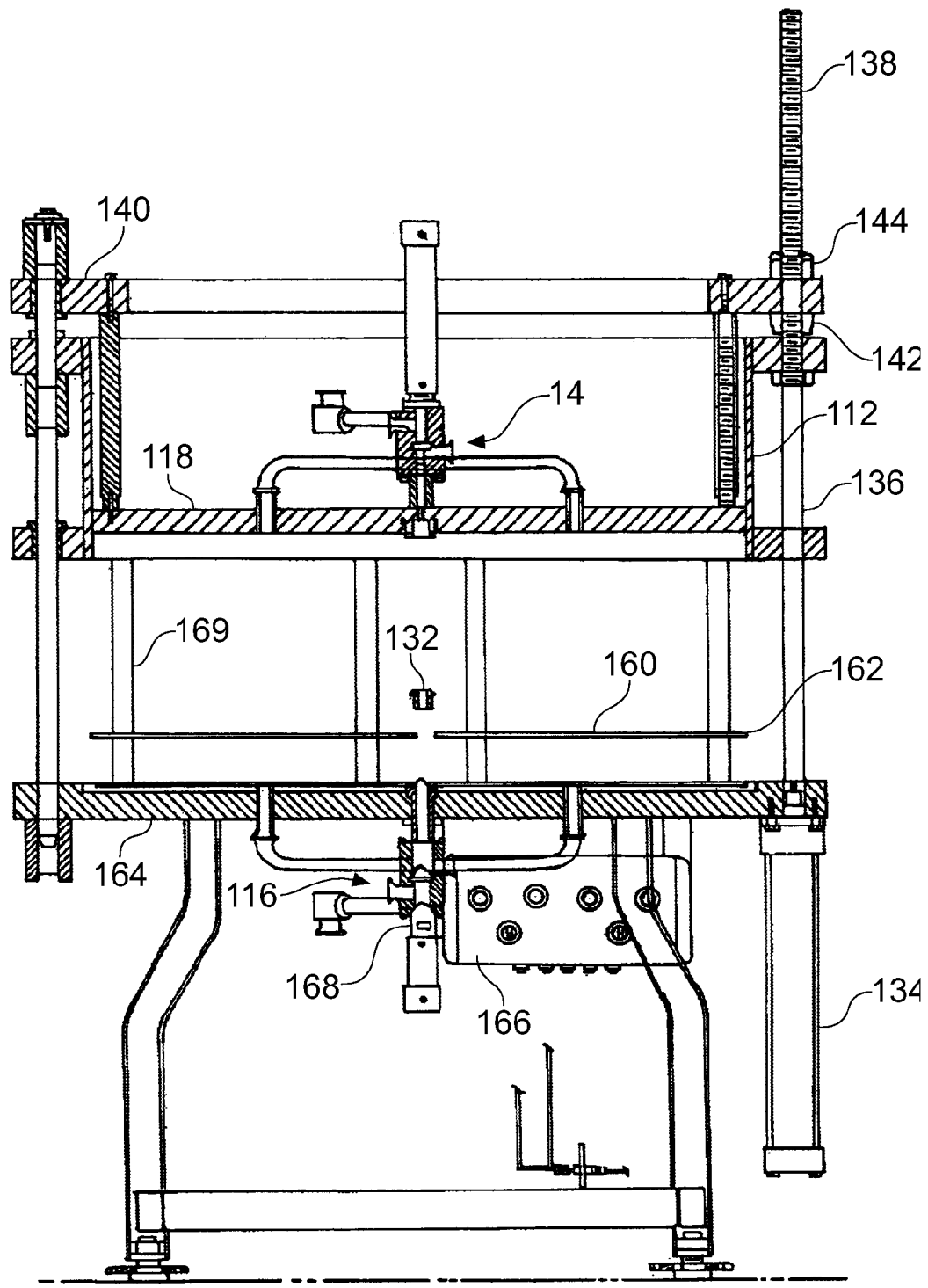
FIG. 2 is a cross sectional view showing the same embodiment of the column of FIG. 1 in a second maintenance position.

In order to perform a second maintenance operation, such as removal of the lower bed support or screen 160 which is typically positioned so that its outer edge 162 is between the tube 112 and the collection system 116, the tube 112 may be raised by the drive system as illustrated in FIG. 2. The bolts which normally secure the tube 112 to the base 164 are removed, and the nuts 142, 144 may be coupled to the piston 136 to drive the tube 112 along with the drum 118 upwards as shown. A gap is thus provided which allows access for an operator to loosen nut 132, which affixes the lower bed support/screen 160 to the base 164, and remove the bed support 160 manually for maintenance. Once maintenance has been completed, the bed support 160 is manually replaced, affixed by nut 132 to the base 164 by the operator, and the process reversed to lower tube 112 and the drum 118 into an operational position.

Although not described below, it will be understood that the maintenance of the column described in FIGS. 1 and 2 could be carried out in accordance with the present invention.

The present invention will now be described with reference to FIGS. 3 to 16; FIGS. 3 to 8 relate to providing access to the upper adapter assembly, FIGS. 9 to 14 to providing access to the base assembly for maintenance and FIGS. 15 and 16 to the use of the handling device of the invention in carrying/lifting other column components not described in the preceding figures.

Figure 3:
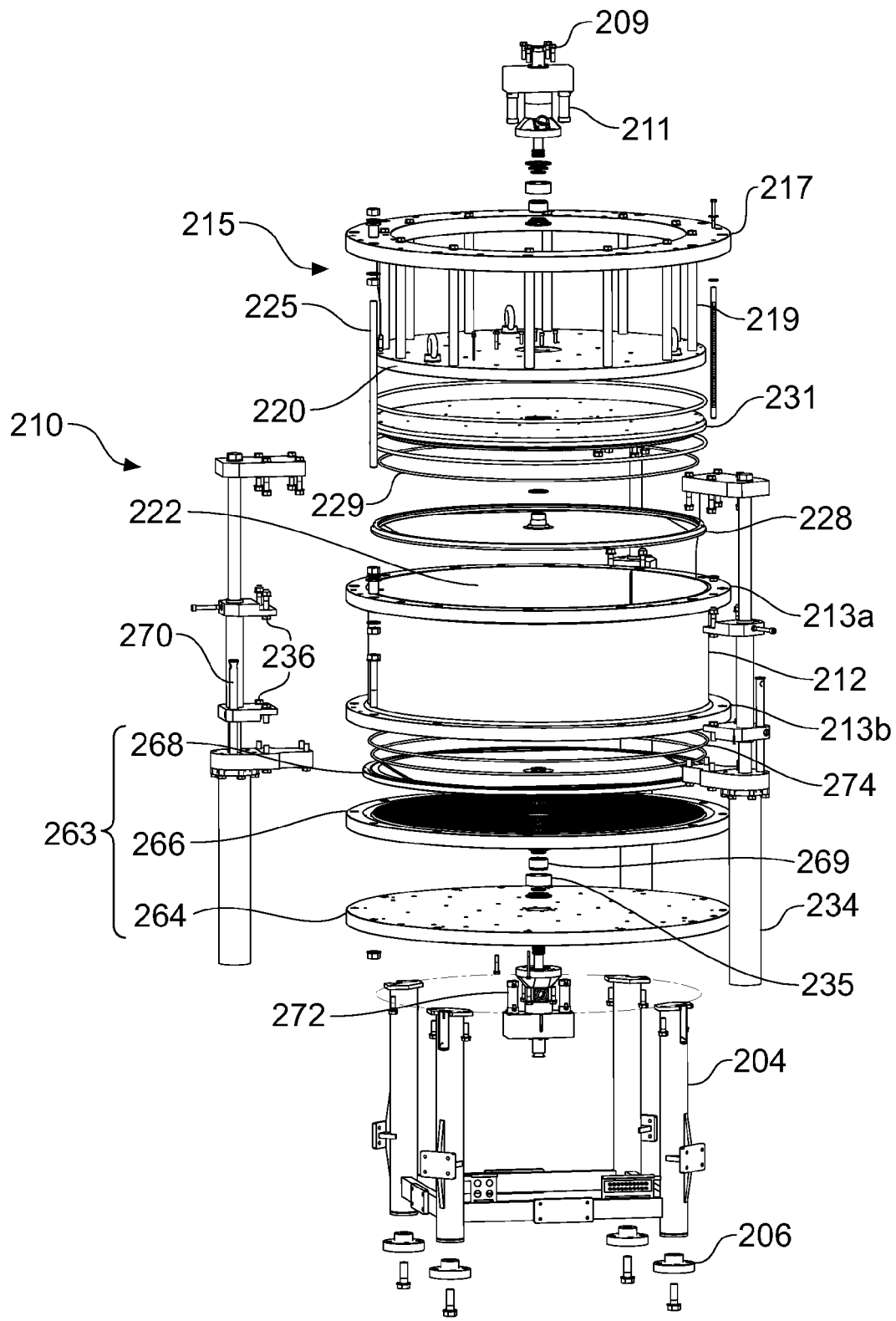
FIG. 3 is a schematic exploded front view of a column described in applicant's U.S. patent application Ser. No. 11/763,477.

FIG. 3 is a schematic exploded front view of a column described in applicant's U.S. patent application Ser. No. 11/763,477. The column is made of strong, inert materials such as stainless steel and other materials which are suitable for use in a GMP environment typical of the pharmaceutical industry. The column 210 is supported on legs 204 having feet 206 which are adjustable in order to modify the height and/or the level of the column. The legs 204 support the column 210 which comprises a cylindrical housing or tube 212 separating a base assembly 263 at one end from an adapter assembly 215 at the other. The tube 212 may typically be made from stainless steel, or other strong, inert materials. Adjacent to the adapter assembly 215 is a dispersion system comprising a nozzle 211 which includes a mobile phase pathway, for the introduction of buffer or other suitable mobile phase liquids or chemicals/materials to be separated, and a liquid inlet 209. The tube 212 may be connected to the adapter assembly 215 and base assembly 263 by a drive system having one or more cylinders 234. The drive system may be a hydraulic system, as shown, or may be powered by other suitable means, such as pneumatic or electrical means. The adapter assembly 215 is moveable within a cavity 222 of the tube 212 in an operational mode, for example, to pack or compress the bed of chromatographic media used to effect chromatographic separation of chemicals within the column. The adapter assembly 215 comprises an adapter flange 217, one or more distance pillars 219, a backing plate 220 made typically of stainless steel, a distributor 231 which may take the form of a plate having many channels to effect the even distribution of liquids, and a bed support 228 comprising a screen or mesh or filter and optionally a sealing ring (e.g. 229). The bed support may be made of an inert plastic or metal material such as stainless steel. The distributor 231 and bed support 228 are fastened to each other by releasable fixing means (not shown). Typical releasable fixing means include, but are not limited to, a screw, a nut or a clamp. The fixing means 230 may only be accessed and thus released from the exterior face of the backing plate 220, that is the face of the plate furthest away from the cavity 222. In the present example, the nozzle 211 must first be removed to provide access to the fixing means 230. Additional releasable fixing means, accessible from the exterior face of the backing plate, may optionally be employed to fasten the backing plate, distributor and bed support together. These fixing means can take the form of bolts inserted through corresponding holes around the perimeter of the components. Access from the exterior face of the backing plate avoids unnecessary exposure of the operator to a suspended or supported load within the column.

The base assembly 263 comprises a backing plate 264 together with a distributor 266 and a bed support 268 fastened to each other by releasable fixing means 269. The bed support 268 comprises a screen or mesh or filter and optionally a sealing ring (e.g. 274). The bed support may be made of an inert plastic or metal material such as stainless steel. Releasable fixing means 269 are, for example, a screw, a nut, a bolt or a clamp; it will be appreciated that other releasable fixing means are also possible. As can be seen from the figure, the fixing means 269 secures bed support 268 and the distributor 266 through a central hole in each component. The fixing means 269 is only accessible and may therefore only be released from the exterior face of the backing plate 264. In FIG. 3, nozzle 272 must first be removed to provide access to release fixing means 269. Additional releasable fixing means, accessible from the exterior face of the backing plate, may optionally be employed to fasten the distributor and bed support together. These fixing means can take the form of bolts inserted through corresponding holes around the perimeter of the components. Access from the exterior face of the backing plate 264 avoids operator exposure beneath a suspended load, were access only to be available from within the interior of the column.

It will be understood that separation of chemical or biological materials on the column, when the tube 212 is full of chromatographic media, can be carried out in either a downward or upward flow. Thus, in a downward flow, liquid containing chemical or biological materials to be separated is introduced through nozzle 211 and moves in a downward direction through the bed of media, to be collected in the collection system at the base of the column via an outlet port (not shown). In upward flow mode, liquid containing materials to be separated is introduced via the bottom nozzle 272 and flows upwards through the media bed to be collected at the top of the column via an outlet port (not shown). In the interests of clarity, the maintenance or servicing of the column will be described in downward flow mode.

In order to conduct maintenance on the adapter assembly 215 or distributor 231, the adapter assembly 215 is disconnected from the column tube 212 by unscrewing the nuts which join the adapter flange 217 to the upper column flange 213a. The drive system then raises the adapter assembly 215 by means of cylinders 234 to allow for access to the interior of the column for maintenance or service. The adapter assembly 215 is locked into position by means of locking rods 225 which are aligned with and screwed into threaded holes in the locking system 270. In this secured position, the adapter bed support and/or the distributor may be removed from the column with a handling device (not shown) for maintenance once the fixing means are released, release being effected by removal from the exterior face of the column following removal of the nozzle 211 as described above. Once maintenance has been carried out on the column (e.g. the bed support 228 has been replaced by means of the handling device), the column 210 is made operational again by reversing the above procedure: the adapter assembly 215 is released from the locking rod 225 and lowered by use of cylinders 234, and then reconnected to the column tube 212 by replacing the nuts which join the adapter flange 217 to the upper column flange 213a.

Maintenance or service is carried out on the bottom distributor 266 or base assembly 263 by releasing the tube 212 from the base assembly 263 and lifting the tube 212 and adapter assembly 215 with the aid of the drive system. The bolts on the lower flange 213b of the column tube 212 which join it to the bottom backing plate 264 are removed. The column tube 212 and adapter assembly 215 are then lifted by means of the drive cylinders 234. The tube 212 and upper adapter assembly is secured in position above the base with the cylinder brackets 236 by screwing locking bolts through holes aligned in the locking pin 270, bracket 236 and cylinder 234.

The bottom nozzle 270 is then disconnected from the back plate 264 and distributor 266. The nozzle 270 is removed together with the distance ring 235, to allow access to release the fixing means 269 which may be in the form of a nut. The nut 269 is removed from the exterior face of the backing plate 264, i.e. the face distant from the cavity 222, and thus eliminates operator exposure to a suspended or supported load. If additional releasable fixing means, such as bolts inserted through the backing plate, distributor and bed support as described above are present, these must be removed from the exterior face of the backing plate. The interior of the column may now be accessed for maintenance or service, such as the replacement or cleaning of the bed support 268 and/or O-rings, the bed support being removed with the aid of a handling device (not shown). To return the column to an operational mode, the above procedure is reversed.

Figure 4B:
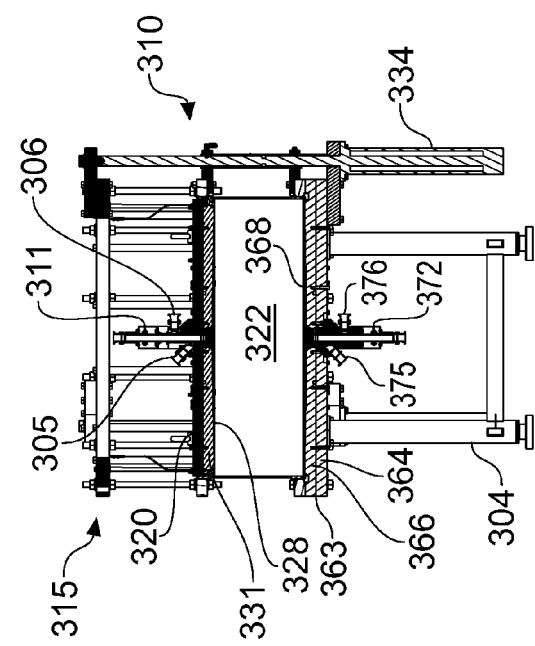
Figure 4A:
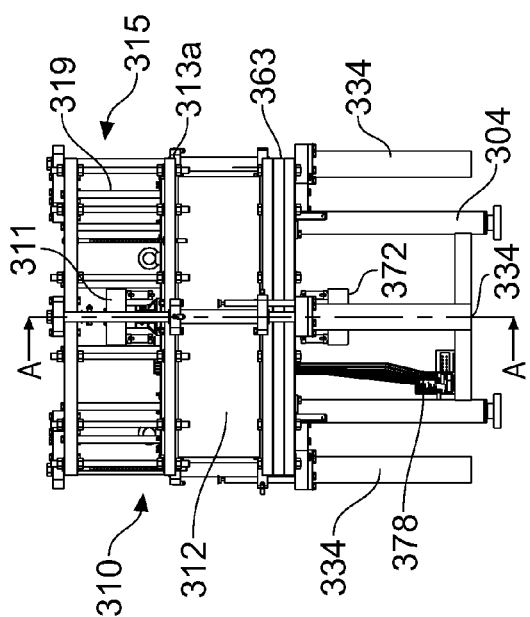
FIG. 4a is a schematic front view of a column described in U.S. patent application Ser. No. 11/763,477.

FIG. 4a is a schematic front view of a column of FIG. 3. The column 310 is supported on legs 304 and has a base assembly 363 separated from an adapter assembly 315 by a tube 312. These components are made of strong, inert materials which are approved for GMP within the pharmaceutical industries, such as stainless steel. In the figure, the base assembly 363 and adapter assembly are connected to a drive system which takes the form of three hydraulic cylinders 334. It will be understood that in other embodiments, different drive systems may be used to raise and lower the column, such as those powered by compressed air or electricity. Furthermore, it is not essential that three cylinders are used, in some cases one being sufficient. The column 310 has a top nozzle 311 and a bottom nozzle for the introduction of liquids into the column. An electrical unit 378 for controlling the drive system is also shown.

FIG. 4b is a side sectional view of the column of FIG. 4a showing one of the hydraulic cylinders 334 in cross section. The cavity 322 for containing the bed of chromatographic media can be seen in cross section. The liquid inlet 305, 375 and outlet 306, 376 of the top 311 and bottom 372 nozzle are shown, for the introduction and removal of liquids from the column 310. The cylinder 334 is connected to the base assembly (comprising backing plate 364, distributor 366 and bed support 368) and the adapter assembly 315 (comprising backing plate 320, distributor 331 and bed support 328).

Figure 4C:
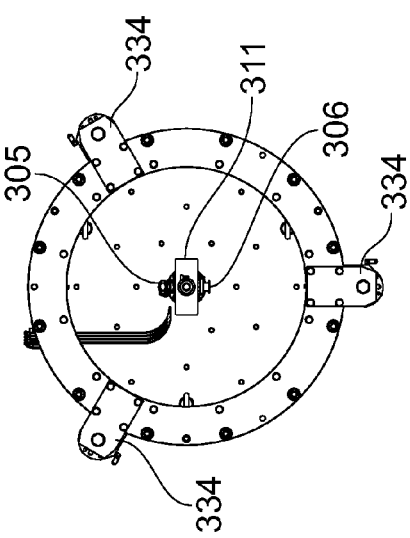

FIG. 4c is a top plan view of the column of FIG. 4a which shows the three hydraulic cylinders 334 and nozzle 311 with liquid inlet 305 and outlet 306.

To raise the adapter assembly 315 for maintenance purposes, the nuts under the upper column flange, which join the adapter 315 and column flange 313a, are loosened and removed. The drive system then lifts the adapter assembly 315 by means of the hydraulic cylinders 334. The adapter assembly 315 is raised until the locking bolts are opposite the threaded holes in the hydraulic cylinders 334 and the bolts screwed in to secure the assembly in the service or maintenance position (see FIG. 3).

Figure 5A:
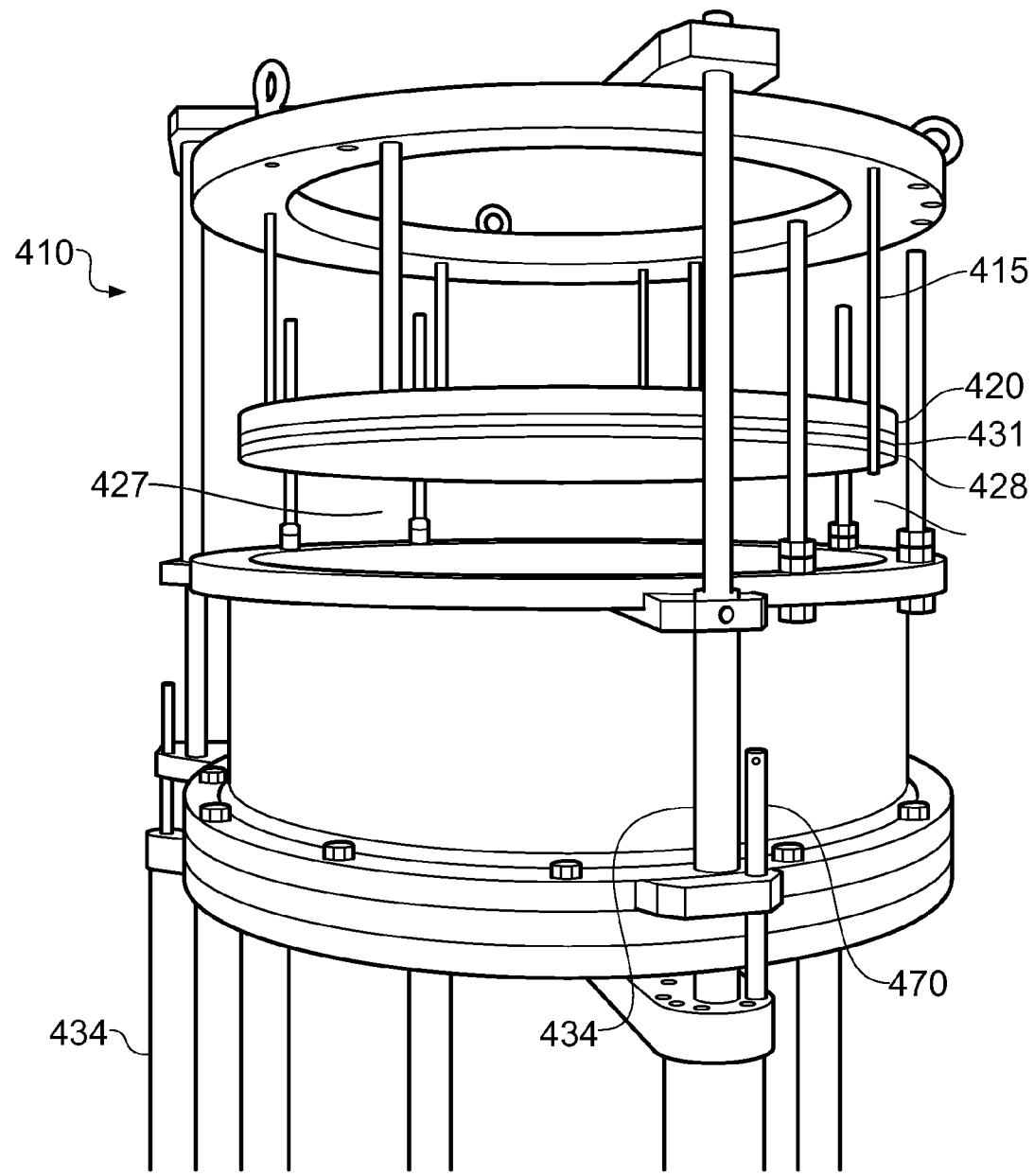
FIG. 5a is a front perspective view showing the adapter assembly raised and secured into position to provide a gap for access.

FIG. 5a is a front perspective view showing the adapter assembly 415 raised and secured into position to provide a gap 427 for access to the interior of the column for service or maintenance. The column 410 has a drive system comprising three hydraulic cylinders 434. The adapter bed support 428, the distributor 431 and the backing plate 420 are now visible; the bed support 428 can be unfastened from the distributor 431 by releasing the fixing means (not shown) without accessing the gap 427. In order to describe this process, reference is made to FIG. 4 in that the nozzle 311 is first removed to provide access to remove the retaining nut (not shown) which secures bed support 328 to the distributor 331 without accessing the gap 427. The fixing nut is removed from the exterior face of the backing plate 320.

Figure 5B:
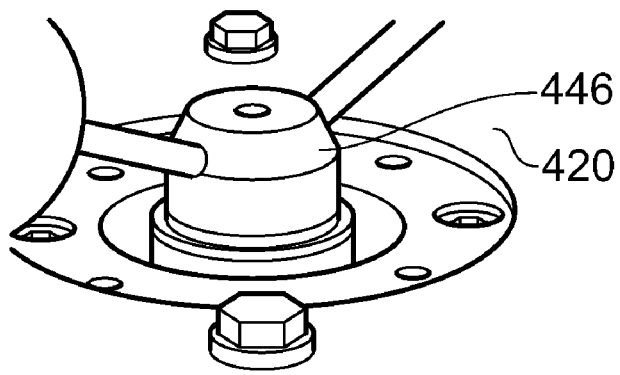
FIG. 5b shows removal of the fastening means securing the backing plate to the distributor and bed support.

FIG. 5b shows release of the fixing means from the backing plate 420 side of the adapter assembly using a spanner 446. The fixing means (in the form of a retaining nut, obscured by the spanner) secures the adapter bed support to the distributor.

The bed support 428 is heavy and requires the use of a handling device to lift it once it has been separated from the adapter assembly.

Figure 6:
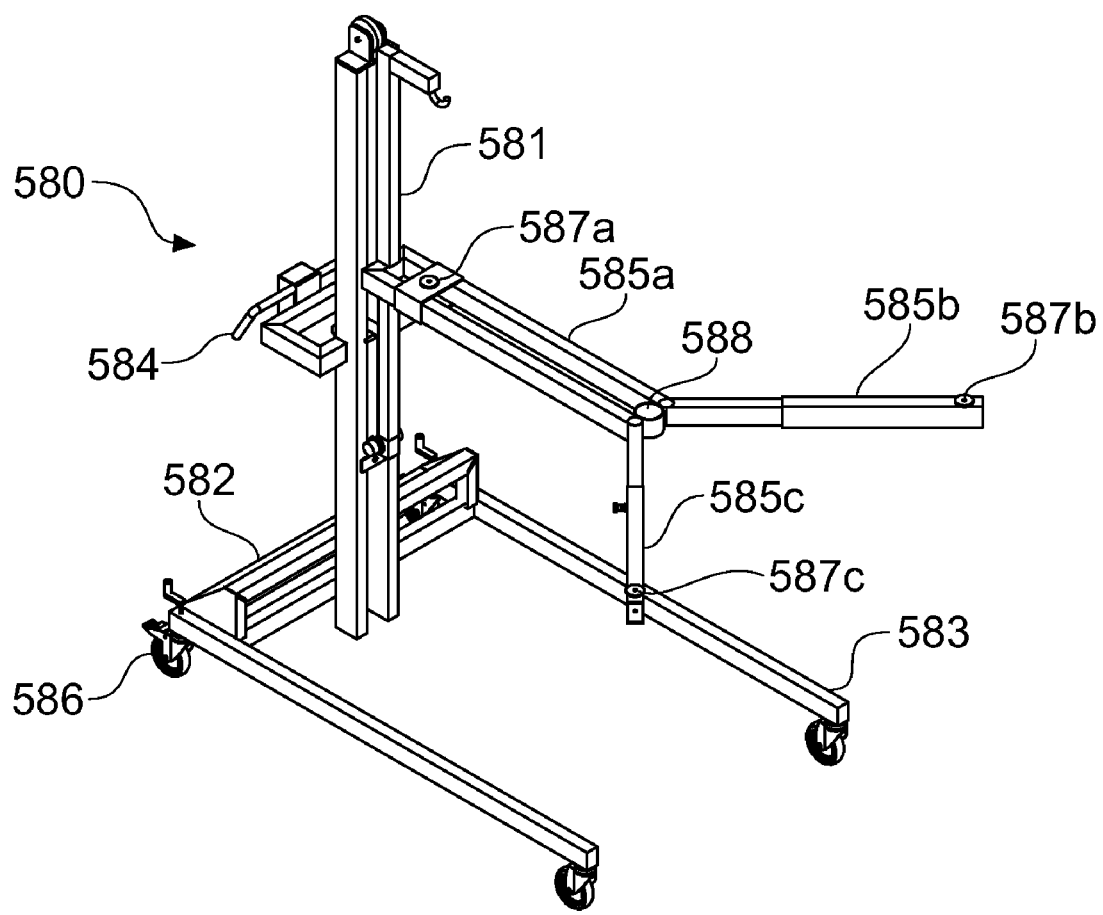
FIG. 6 is a perspective view of a handling device used to remove/insert a distributor or a bed support from/into a column in accordance with the method of the invention.

An embodiment of the handling device 580 is shown in FIG. 6. The device 580 is in the form of a trolley or cart with a vertical pillar 581 supported on frame 582 having legs 583. The device 580 is made of strong, inert materials; such materials include, but are not limited to, stainless steel and other materials which are suitable for use in a GMP environment typical of the pharmaceutical industry. Extendable arms 585a, b, c project from the pillar 581 and can be raised or lowered relative to the pillar 581 by mechanical or other means. In the embodiment shown, the arms 585a, b, c are raised or lowered by a manual jacking mechanism (not shown) adjacent to the handle 584 which provides the means to steer or control the device. The arms 585a, b, c are designed to bear the weight of the distributor or bed support and are extendable to the diameter of these components. While the embodiment shown has three arms 585a, b, c, it will be understood that the device is not so limited and that other embodiments may have less than or more than three arms (e.g. one, two, four, five) depending on the individual design. Each arm 585a, b, c has attachment means for securing a column component thereto. In the embodiment shown, the attachment means comprises a fixture in the form of holes 587a, b, c, at the extremities of the arms 585a, b, c for bolting or securing of the distributor and/or bed support to the arms for safety, particularly during transport, removal and/or insertion of the column component. It will be understood that other attachment means can take many different forms, such as clips, clamps, fasteners etc. Pads (not shown) may be fitted to the arms 585a, b, c to minimise any risk of damage to the bed support/distributor when these components come into contact with the arms. A raised, central element, 588 (typically of conical shape) for receipt of the central hole in the bed support or distributor provides a means for centralising these components on the arms 585a, b, c of the device 580. This element 588 may be fitted on either, or both, the upper or under side of the point where the arms 585a, b, c intersect. In operation, the distributor and/or bed support is either suspended from the arms 585a, b, c or supported on the arms. Pivotal wheels 586 allow easy movement and manoeuvrability of the handling device 580. In the embodiment shown, the movement of the device 580 and the raising/extension of the arms 585a, b, c are by manual means, but it will be understood that other embodiments are possible which incorporate powered systems (e.g. electrical, pneumatic or hydraulic systems) to drive the device 580 and lift/lower the arm 585. It will also be understood that in other embodiments of the handling device (not shown), arm 585a is capable of pivoting or rotation around pillar 581 to enable the arms 585b and c to access a narrow gap between any two cylinders (e.g. 434 of FIG. 5a) and remove/insert a bed support and/or distributor which have a diameter which is greater than the distance between any two cylinders in the column (e.g. 434 of FIG. 5a).

The operation of the device 580 in removing the bed support is shown in FIGS. 7 to 9.

Figure 7A:
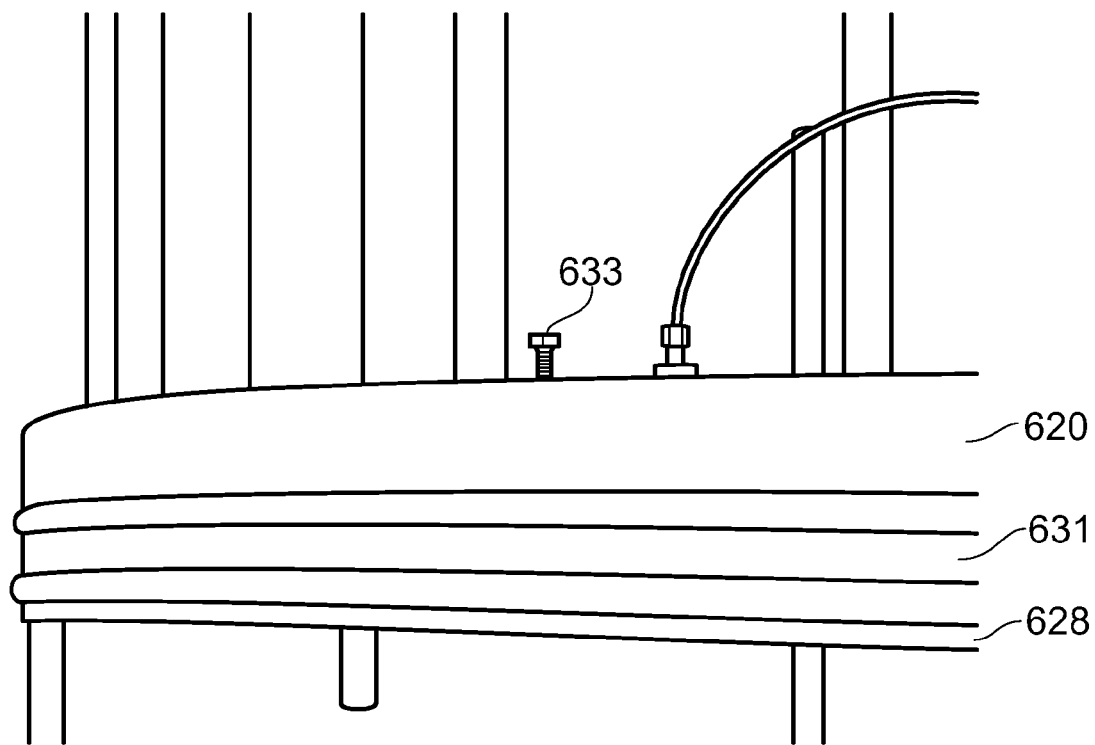
FIG. 7a and FIG. 7b are perspective views of the column of FIG. 5 showing the removal of securing rods which fasten the bed support to the distributor and backing plate.
Figure 7B:
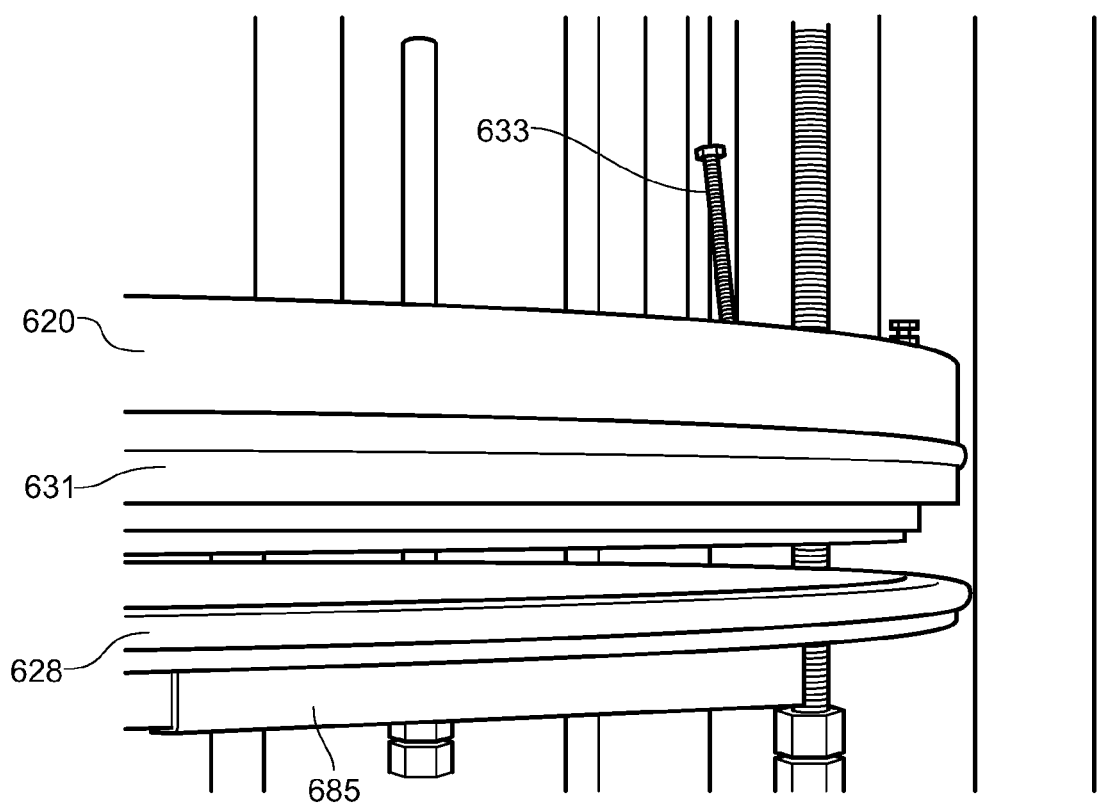

FIG. 7a and FIG. 7b are perspective views of the column of FIG. 5 showing the handling device of FIG. 6 supporting the bed support 628 on one or more arms 685. The arms 685 are raised into position below the bed support 628, care being taken not to damage the mesh of the bed support by positioning the pads (not shown) on the arms 685 of the handling device 680 under the outer rim of the bed support 628, and then gently raising the arms 685 up to the bed support. Once the arms 685 are in position, the nuts on the threaded rods 633 that go through the back plate 620 and distributor 631 into the outer perimeter of the bed support 628 are loosened and the bed support can be removed on the handling device. The rods 633 are initially loosened with a spanner and finally removed by hand. As can be seen from the figures, the removal of the rods 633 is carried out from the exterior face of the backing plate 620 without accessing the gap and thus without exposing the operator to a suspended or supported overhead weight.

Figure 8A:
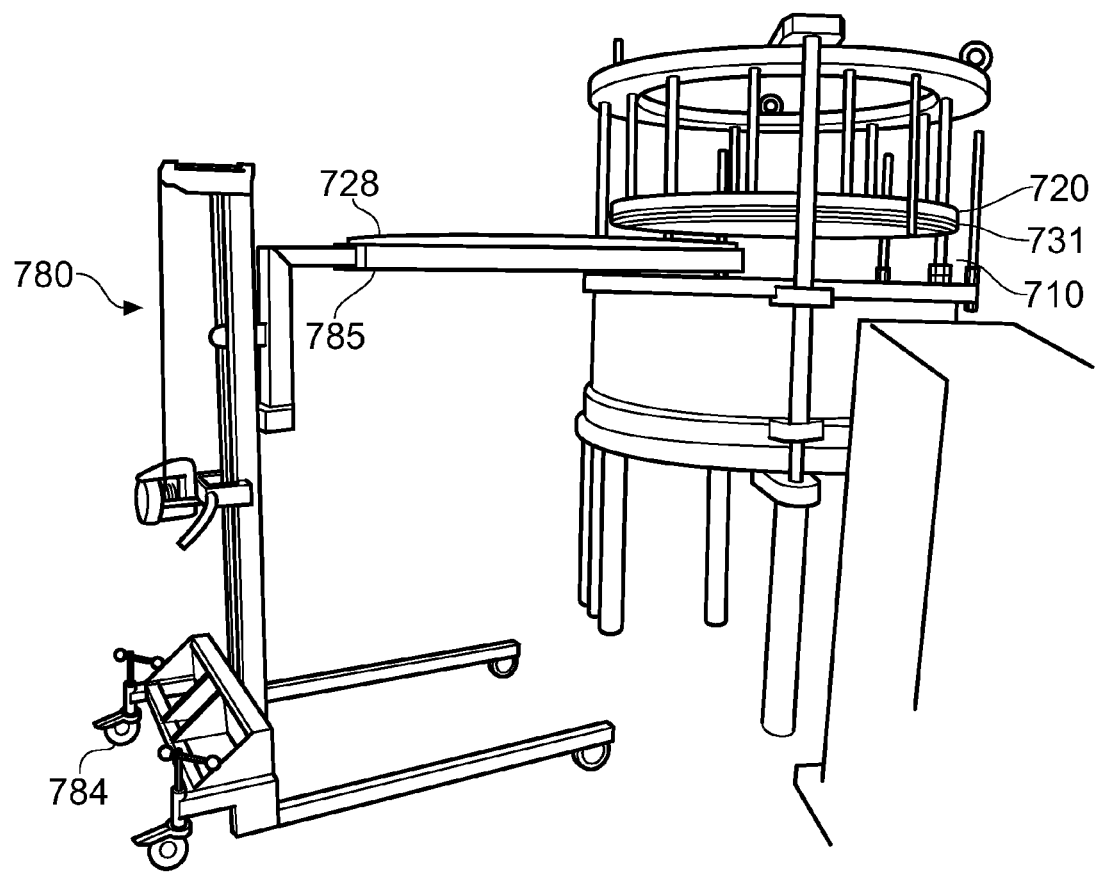
FIG. 8a and FIG. 8b are perspective views showing the removal of the bed support from the column.
Figure 8B:
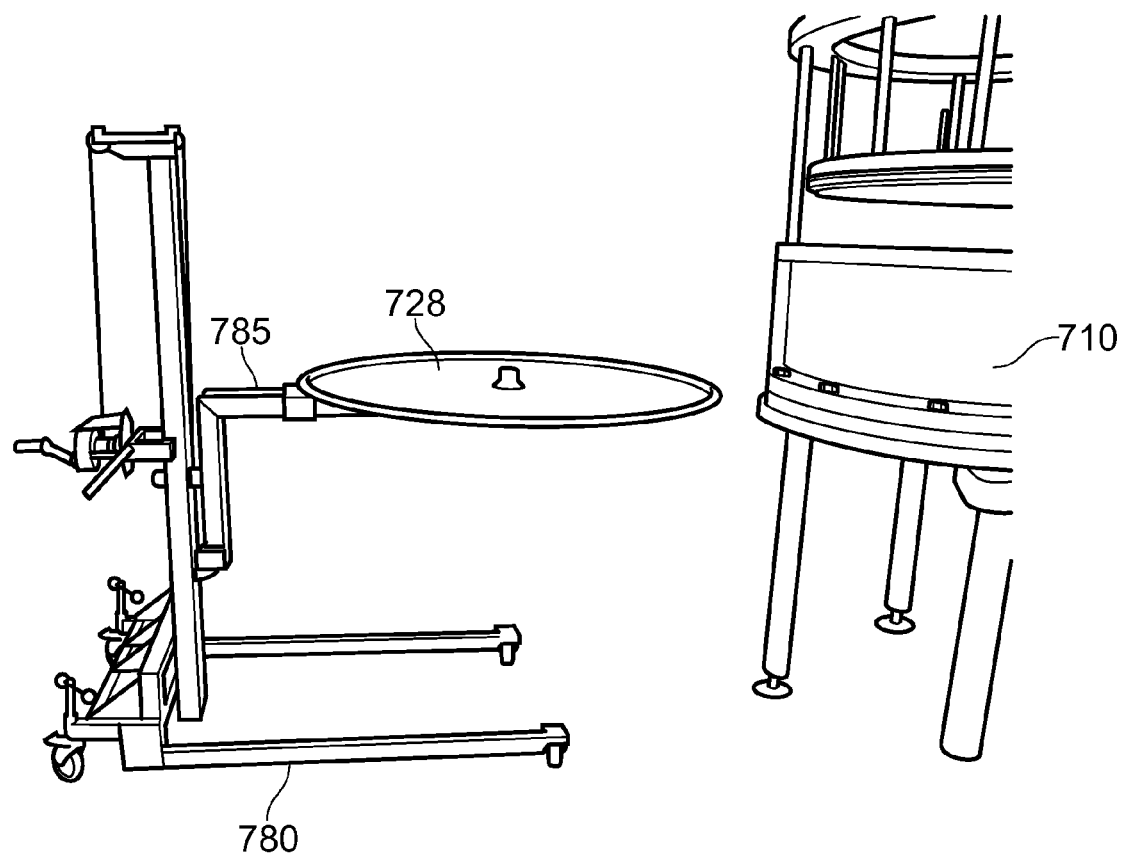

FIG. 8a and FIG. 8b are perspective views showing the removal of the bed support 728 on the handling device 780 from the column 710. In FIG. 8a the bed support 728, borne on the arms 785 of the device 780, is removed from the column 710 without substantially tilting the support 728. The device 780 can then be moved away from the column (FIG. 8b) and the arms 785 lowered in order that the bed support 728 can be cleaned or replaced. Maintenance or servicing the column may now be carried out as required. For example, the bed support 728 may be cleaned or replaced, O-rings replaced and/or the distributor 731 may also be removed for cleaning.

To return to an operational mode, the above procedure is simply reversed. The bed support and distributor are returned to the column and affixed to the backing plate, the nozzle reattached, and the adapter assembly lowered and bolted to the column tube.

Access to the bottom bed support and interior of the column will now be described with reference to FIGS. 9 to 13. To access the bottom bed support, the tube is released from the base assembly by unscrewing the bolts that join it to the base and then lifting the tube and upper adapter assembly with the hydraulic cylinders.

Figure 9A:
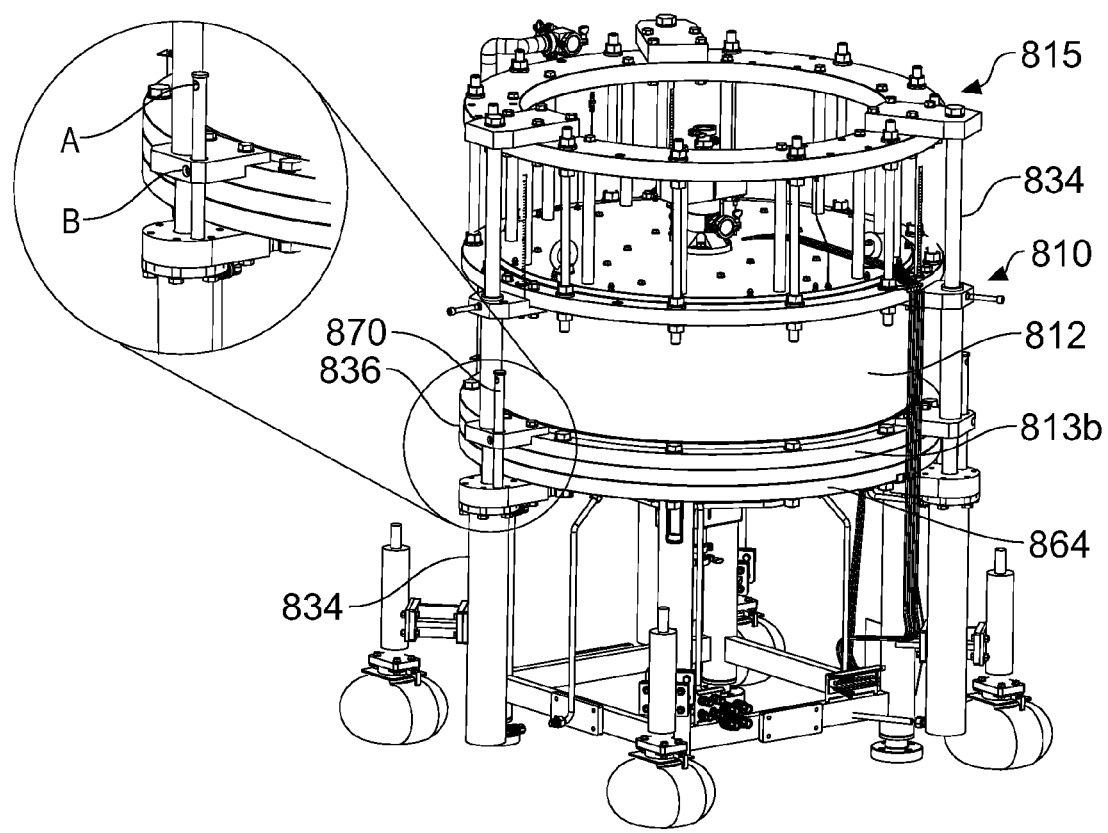
FIG. 9a is a perspective view of a column with an inset showing a locking system.
Figure 9B:
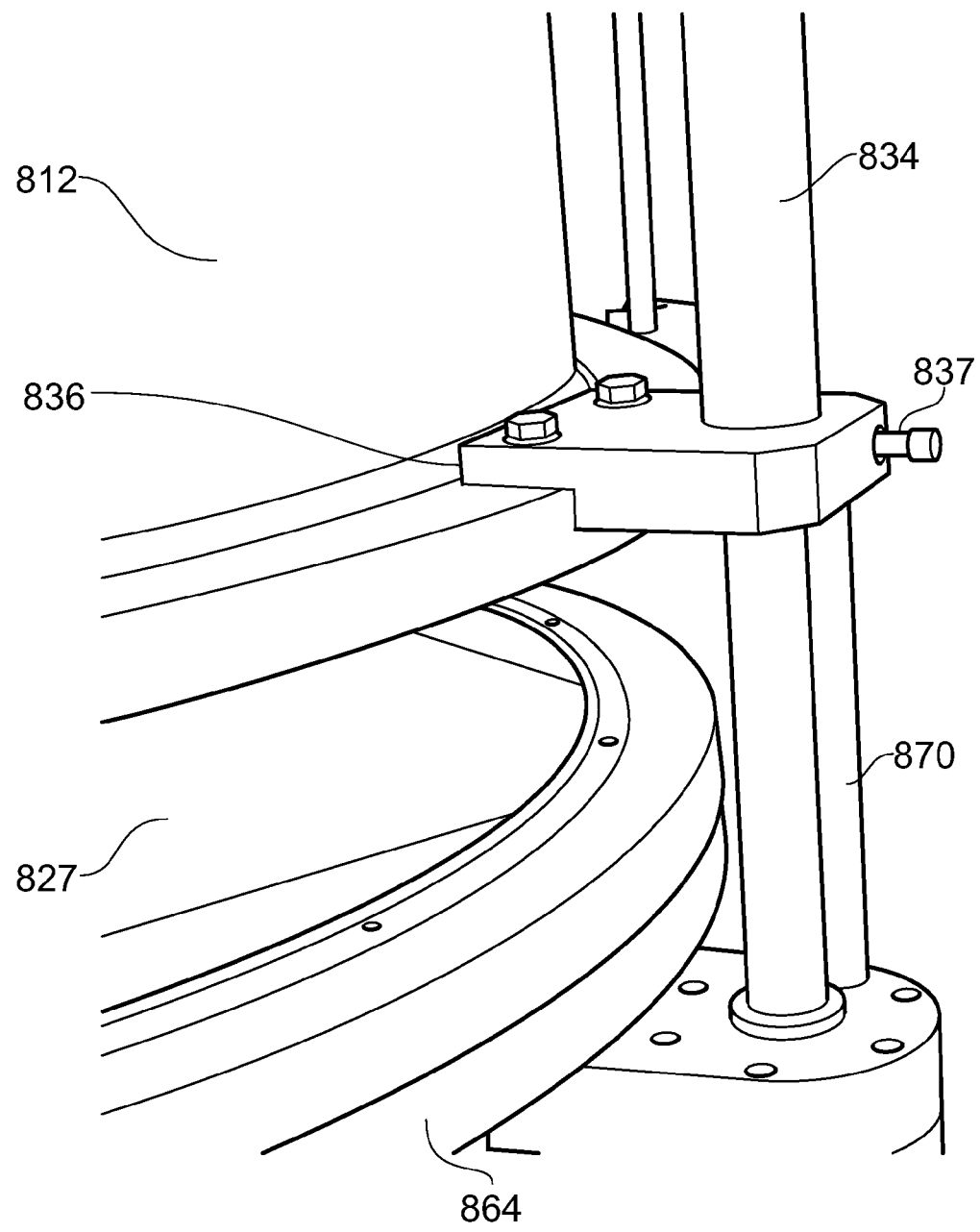
FIG. 9b shows the column tube raised above the base and in the process of being locked into position.

FIG. 9a shows a column 810 as previously described in FIGS. 3 to 5 and FIGS. 7 and 8. The bolts on the lower flange 813b of the column tube which fasten the tube 812 to the bottom backing plate 864 are loosened and unscrewed. The column tube 812 and adapter assembly 815 are lifted by the hydraulic cylinders 834 of the drive system until the hole indicated by 'A' is opposite the hole indicated by 'B' in the inset of FIG. 9a. Locking bolts 837 are then introduced into the aligned holes in the locking pin 870, bracket 836 and cylinder 834 to secure the tube and adapter assembly in position (FIG. 9b). After removal of the bolts securing the tube 812 to the bottom backing plate 864, maintenance can now be carried out on the column in the gap 827 created by raising the tube and adapter assembly.

Figure 10:
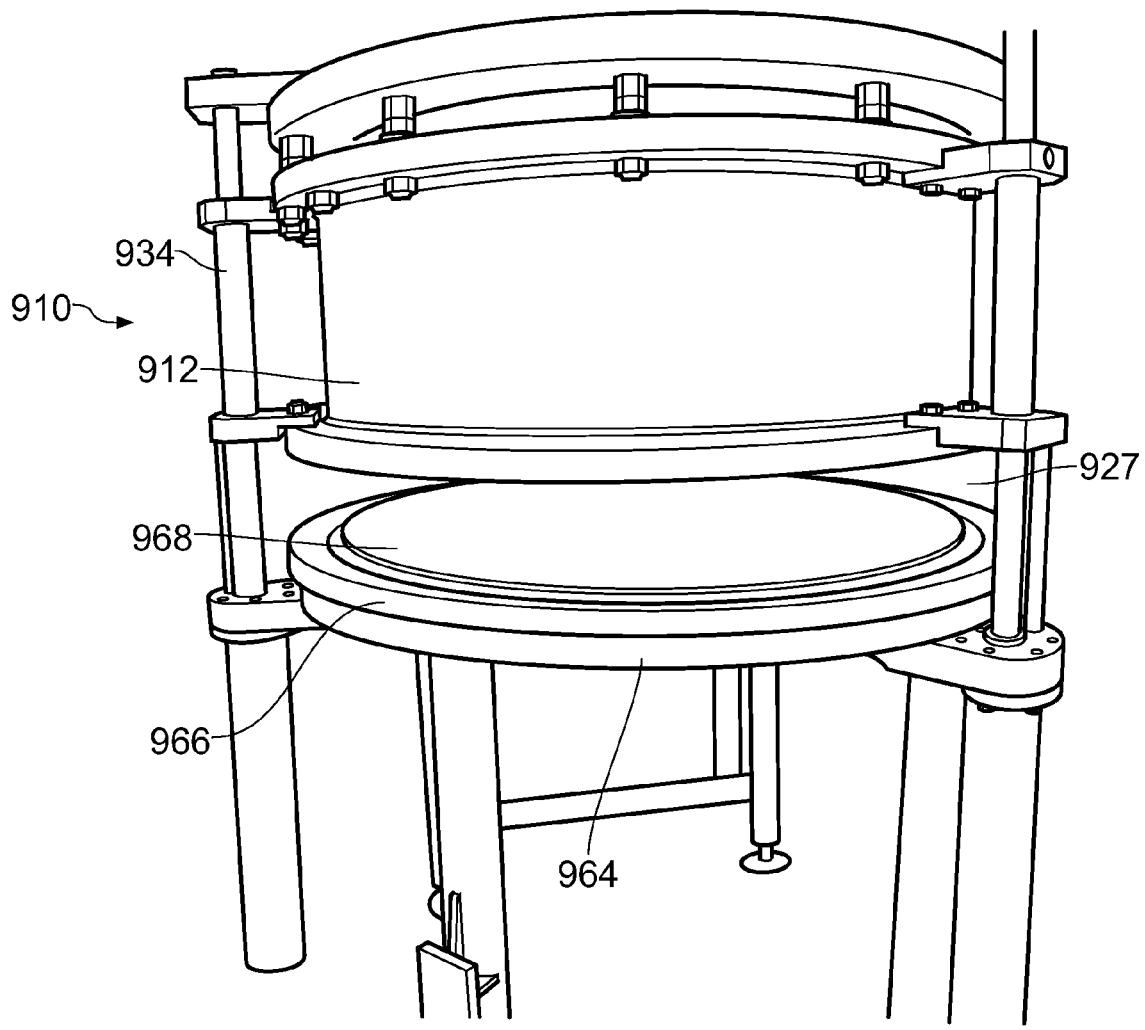
FIG. 10 is a perspective view of a column with the column tube raised and locked into position in readiness for maintenance.

FIG. 10 shows the column 910 with the tube 912 raised and mechanically locked to the cylinders 934 in readiness for maintenance. The bottom nozzle (not shown—see 272 in FIG. 3) is first removed from the back plate 964 by unscrewing the retaining bolts. The retaining nut (or fixing means) which fastens the bed support 968 to the distributor 966 is released from the backing plate 964 side of the column 910. If additional fixing means are present, such as bolts (not shown)

which fasten the bed support to the distributor and the backing plate, and are located on the perimeter of the backing plate, these are released from the backing plate face of the column.

Figure 11A:
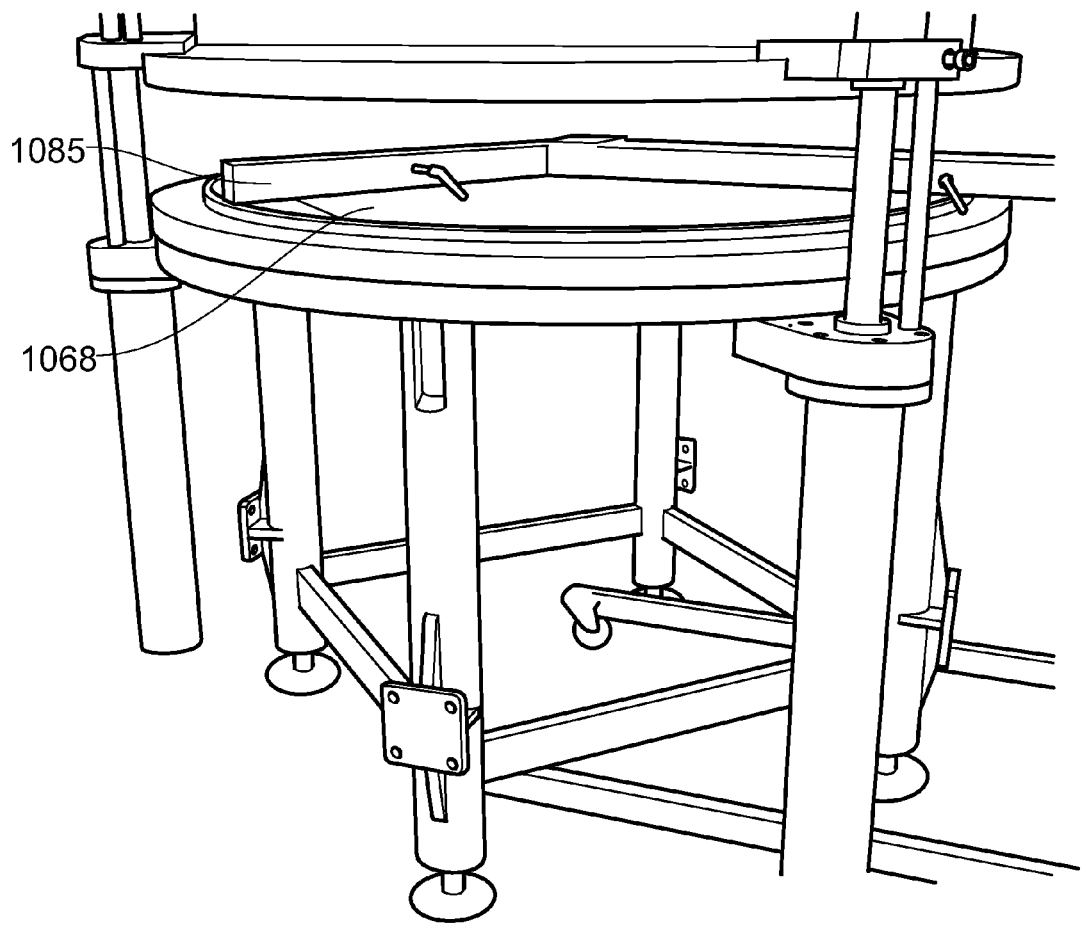
FIGS. 11a and FIG. 11b illustrate the process of removing the bed support from the column using a handling device.
Figure 11B:
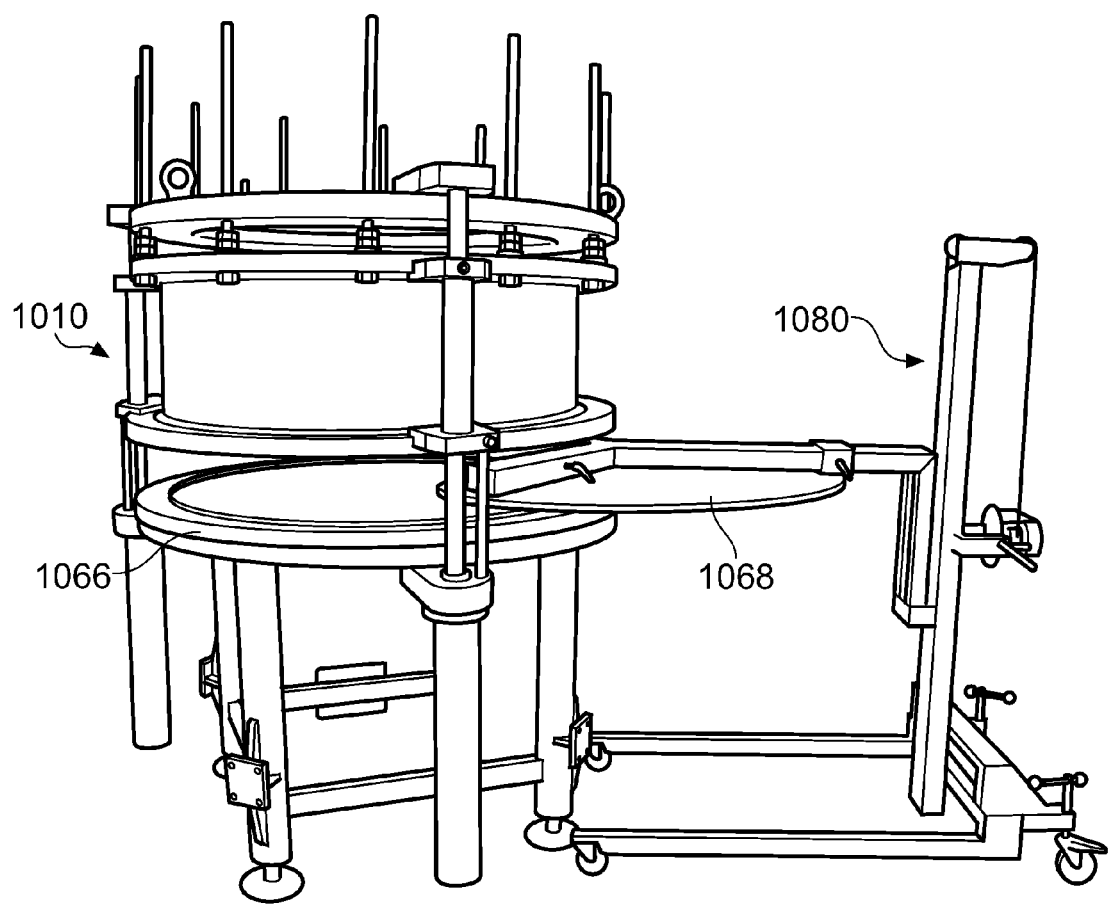
Figure 12:
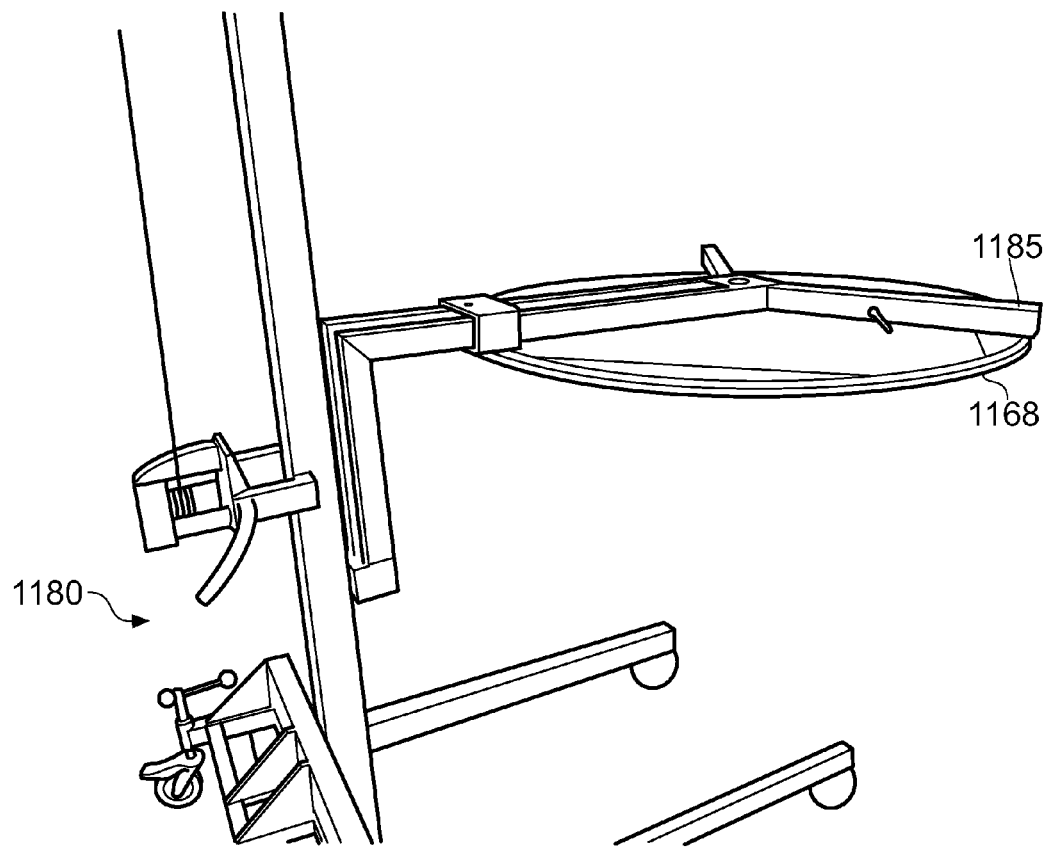
FIG. 12 shows the bed support having been removed from the column in readiness for maintenance.

The bed support 1068 can now be removed from the column by use of the handling device as shown in FIG. 11a and FIG. 11b. The handling device (as described in FIG. 6 above) 1080 is wheeled into position where the arms 1085 are a few centimetres above the bed support 1068. The bed support 1068 has a number of threaded holes that correspond to the holes used to bolt the bed support to the backing plate 1064. The arms 1085 of the handling device 1080 have holes through which bolts are screwed into the bottom bed support 1068; these holes are aligned to those of the bed support 1068 and bolts affixed to secure the bed support to the arms 1085. Once attached, the bed support 1068 can be removed from the column by raising the arms 1085 a few centimetres and wheeling the handling device 1080 away from the column 1010. The bed support 1068 can now be cleaned or new 0-rings replaced as necessary. Generally the bed support will be moved away from the column, as shown in FIG. 12, lowered onto a surface (such as a trolley or workbench) and released from the arms 1185 of the handling device 1180 to facilitate cleaning and servicing. The distributor (1066 in FIG. 11) can also be removed and serviced in a similar manner using the handling device.

Figure 13:
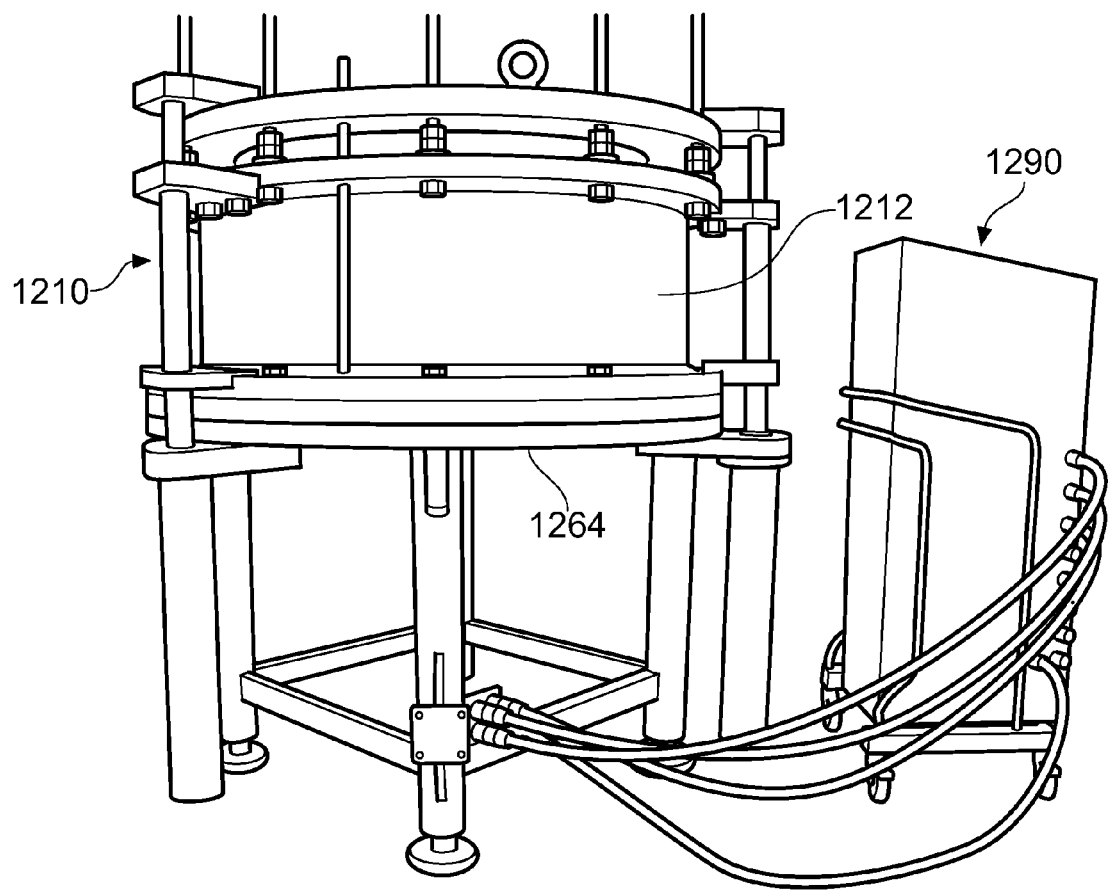
FIG. 13 is a perspective view of the column of FIGS. 10 and 11 with the column tube lowered awaiting bolting to the base.

Once maintenance or servicing has been completed, the column is returned to an operational mode by simply reversing the process as described above. This involves replacing the bed support/and or distributor in the column, affixing the components to the backing plate, reattaching the nozzle, lowering the tube and adapter assembly. FIG. 13 shows the column 1210 of FIG. 11 connected to the hydraulic control unit 1290 with the tube 1212 lowered and ready to be bolted to the backing plate 1264.

Figure 14:
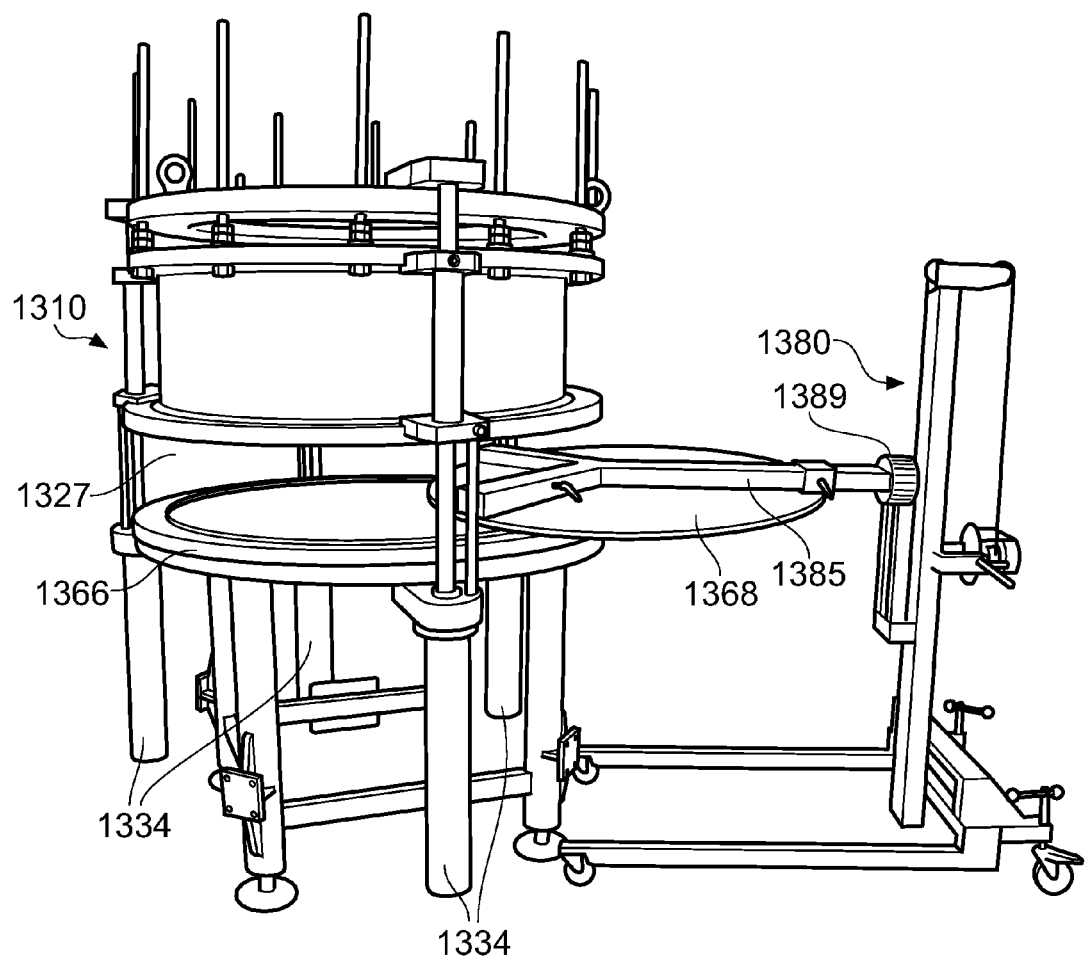
FIG. 14 is a perspective view showing a handling device tilting a bed support to remove it from the gap in a column where the distance between each of the drive cylinders is less than the diameter of the bed support.

FIG. 14 illustrates the removal of a bed support 1368 from gap 1327 of a column 1310 in which the distance between any two drive cylinders 1334 is less than the diameter of the bed support 1368. This is the case for example in the column in FIG. 14 which has four drive cylinders 1334 or in the column described in FIG. 1 and 2. In order to do so, arm 1385 of handling device 1380 is designed to rotate or pivot around joint 1389 and, by so doing, substantially tilt the bed support 1368 such that it can be removed or inserted between the cylinders 1334.

Figure 15:
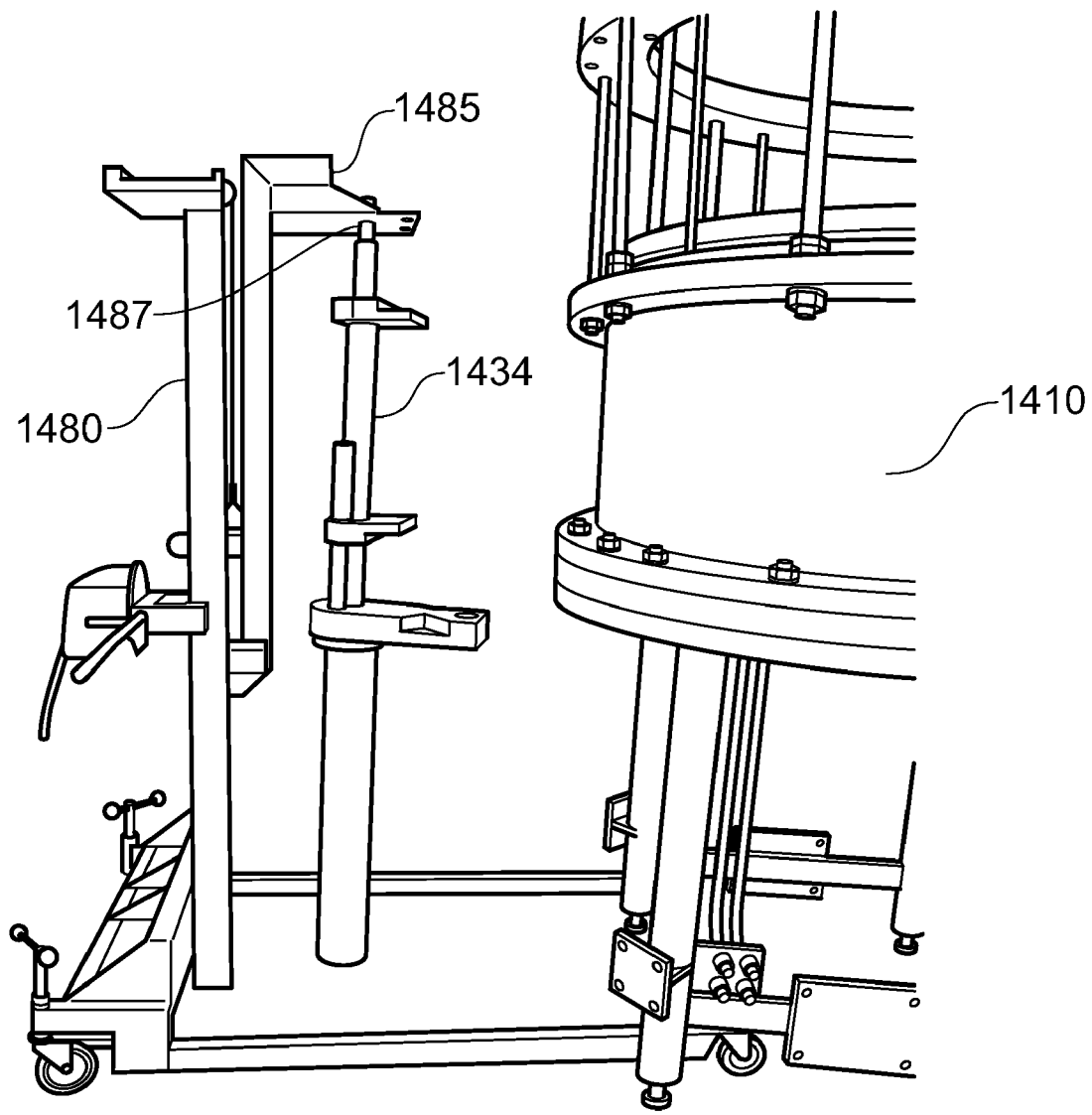
FIG. 15 depicts a handling device carrying a drive cylinder.

The handling device can also be used to remove or replace other column components from/on a column. FIG. 15 illustrates the removal of a drive cylinder 1434 from column 1410 by affixing the cylinder to the arm 1485 of the handling device 1480. The drive cylinder 1434 is secured to the arm 1485 of the handling device 1480 by attachment means 1487 in the form of screw holes for the receipt of the drive cylinder.

Figure 16:
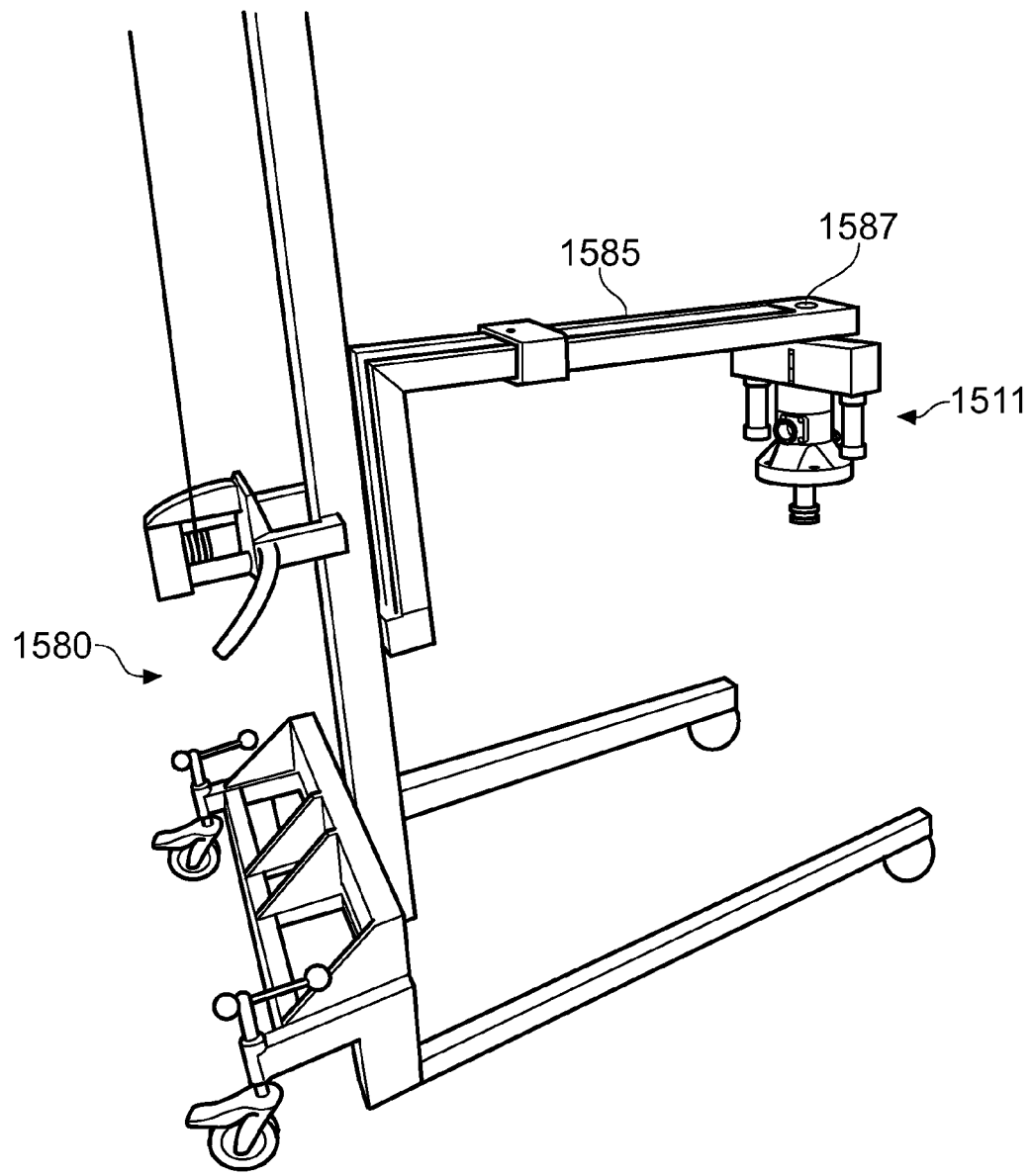
FIG. 16 shows a handling device supporting a nozzle which has been removed from a column.

The nozzle 1511 can also be removed or affixed to the column by the use of the handling device 1580, as shown in FIG. 16. The nozzle is secured to the arm 1585 of the handling device 1580 by attachment means 1587 and may then be transported to and/or lifted away from the column.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A method for conducting maintenance on a chromatography column comprising:
    a) providing a chromatography column comprising:
        a dispersion system comprising a nozzle including a mobile phase pathway connected to a liquid inlet;
        a tube with an adaptor assembly, said adapter assembly moveable within a cavity of said tube in an operational mode;
        the adapter assembly comprising a distributor and a bed support fastened to each other by releasable fixing means;
        a collection system opposing the dispersion system; and one or more seals;
    b) disconnecting the adapter assembly from the tube;
    c) lifting the adapter assembly above the tube to provide a gap for access therebetween;
    d) unfastening the bed support from the distributor by releasing the fixing means;
    e) removing the bed support from the column with a handling device;
    f) conducting maintenance on the column and/or the bed support and/or said one or more seals;
    g) returning the bed support to the column with said handling device and fastening the bed support to the distributor; and
    h) lowering the adapter assembly to an operational position within the tube and reconnecting the adapter assembly to the tube.

2. The method of claim 1, further comprising removing the distributor from the column with the handling device and conducting maintenance on the column and/or said distributor.

3. The method of claim 1, further comprising removing said nozzle from the column with the handling device prior to step d) and returning the nozzle to the column with the handling device following step g).

4. The method of claim 1, wherein said handling device is in the form of a cart having a pillar and comprising one or more arms projecting from said pillar for supporting the bed support or the distributor or the nozzle thereon.

5. The method of claim 4, wherein said arms are extendable from the pillar.

6. The method of claim 4, wherein the arms are vertically movable on the pillar.

7. The method of claim 1, wherein lifting the adapter assembly in step c) and/or lowering the adapter assembly in step h) is carried out by means of an overhead hoist or crane.

8. The method of claim 1, wherein lifting the adapter assembly in step c) and/or lowering the adapter assembly in step h) is carried out by means of a drive system comprising one or more cylinders which are mounted to or are integral with the column.

9. The method of claim 8, further comprising removing said one or more cylinders from the column with the handling device.

10. The method of claim 1, wherein the step of removing the bed support from the column and/or the step of returning the bed support to the column is carried out without substantially tilting the bed support.

11. The method of claim 1, wherein the step of removing the bed support from the column and/or the step of returning the bed support to the column is carried out by tilting the bed support at an angle of more than 5° to the horizontal.

* * * * *